US010299858B2

(12) United States Patent
McLawhorn

(10) Patent No.: US 10,299,858 B2
(45) Date of Patent: May 28, 2019

(54) VARIABLE THICKNESS ELECTROSURGICAL SNARE

(71) Applicant: Cook Medical Technologies LLC, Bloomington, IN (US)

(72) Inventor: Tyler Evans McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 556 days.

(21) Appl. No.: 14/971,557

(22) Filed: Dec. 16, 2015

(65) Prior Publication Data

US 2016/0175042 A1    Jun. 23, 2016

Related U.S. Application Data

(60) Provisional application No. 62/095,984, filed on Dec. 23, 2014.

(51) Int. Cl.
*A61B 18/12* (2006.01)
*A61B 18/14* (2006.01)
(Continued)

(52) U.S. Cl.
CPC ........ *A61B 18/1492* (2013.01); *A61B 18/082* (2013.01); *A61B 18/14* (2013.01); *A61B 2018/00071* (2013.01); *A61B 2018/00077* (2013.01); *A61B 2018/00083* (2013.01); *A61B 2018/00214* (2013.01); *A61B 2018/00589* (2013.01); *A61B 2018/00601* (2013.01); *A61B 2018/00607* (2013.01);
(Continued)

(58) Field of Classification Search
CPC ... A61B 18/082; A61B 18/14; A61B 18/1492; A61B 2018/00071; A61B 2018/00077; A61B 2018/00083; A61B 2018/00214; A61B 2018/00589; A61B 2018/00601; A61B 2018/00607; A61B 2018/00982; A61B 2018/141; A61B 2018/1465; A61B 2018/1497
See application file for complete search history.

(56) References Cited

U.S. PATENT DOCUMENTS 4,493,320 A    1/1985 Treat
4,643,187 A *  2/1987 Okada ................... A61B 18/14
                                                         606/47
(Continued)

FOREIGN PATENT DOCUMENTS

DE    100 28 413 A1    9/2001
DE    20 2010 005677 U1    10/2011
(Continued)

OTHER PUBLICATIONS

Search Report and Written Opinion for corresponding application No. PCT/US2015/066644 dated Apr. 12, 2016.

*Primary Examiner* — Daniel W Fowler
(74) *Attorney, Agent, or Firm* — Brinks Gilson & Lione

(57) ABSTRACT

An electrosurgical snare may include a conductive distal loop that includes an uninsulated thinner portion and an uninsulated thicker portion. Respective current densities over the outer surfaces of the thinner and thicker portions may cause the uninsulated thinner portion to immediately begin cutting tissue, while the uninsulated thicker portion may initially begin coagulating the tissue.

4 Claims, 8 Drawing Sheets

(51) Int. Cl.
*A61B 18/08* (2006.01)
*A61B 18/00* (2006.01)

(52) U.S. Cl.
CPC ........... *A61B 2018/00982* (2013.01); *A61B 2018/141* (2013.01); *A61B 2018/1465* (2013.01); *A61B 2018/1497* (2013.01)

(56) References Cited

U.S. PATENT DOCUMENTS

| | | | |
|---|---|---|---|
| 5,078,716 A * | 1/1992 | Doll | A61B 18/14 606/47 |
| 5,269,780 A | 12/1993 | Roos | |
| 5,437,665 A | 8/1995 | Munro | |
| 5,454,370 A | 10/1995 | Avitall | |
| 5,599,349 A | 2/1997 | D'Amelio | |
| 5,980,519 A | 11/1999 | Hahnen et al. | |
| 7,101,378 B2 | 9/2006 | Salameh et al. | |
| 7,713,270 B2 | 5/2010 | Suzuki | |
| 7,749,218 B2 | 7/2010 | Pellegrino et al. | |
| 8,012,153 B2 | 9/2011 | Woloszko et al. | |
| 8,109,926 B2 | 2/2012 | Azure | |
| 2010/0036375 A1* | 2/2010 | Regadas | A61B 17/32056 606/39 |
| 2010/0268205 A1 | 10/2010 | Manwaring et al. | |
| 2011/0106077 A1 | 5/2011 | Yanuma et al. | |
| 2012/0071712 A1* | 3/2012 | Manwaring | A61B 18/082 600/104 |
| 2012/0283723 A1* | 11/2012 | Jenkins | A61B 18/14 606/41 |
| 2013/0338667 A1* | 12/2013 | Daignault | A61B 18/1485 606/47 |
| 2015/0105789 A1 | 4/2015 | Raybin et al. | |

FOREIGN PATENT DOCUMENTS

| | | |
|---|---|---|
| DE | 20 2013 006687 U1 | 11/2013 |
| DE | 10 2013 107437 A1 | 1/2015 |
| JP | 2005 124696 | 5/2005 |
| WO | WO 93/21845 | 11/1993 |

\* cited by examiner

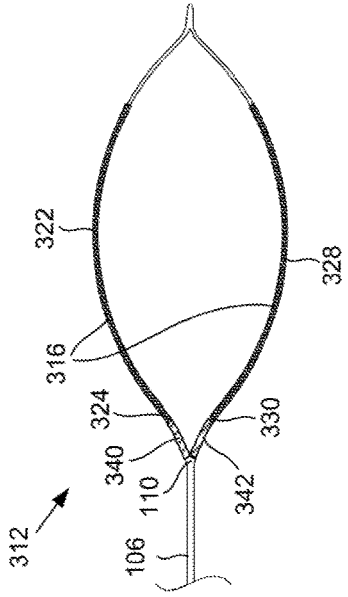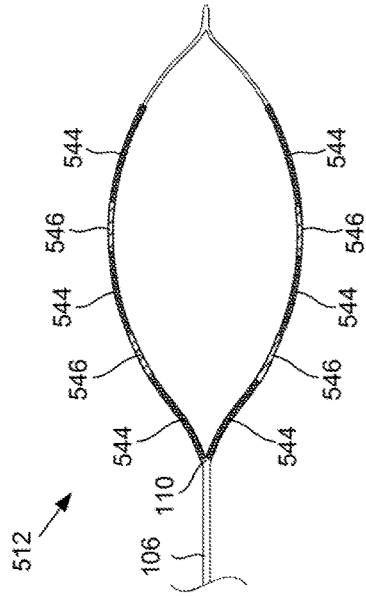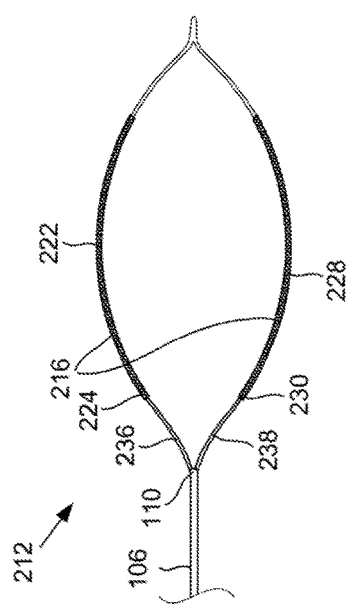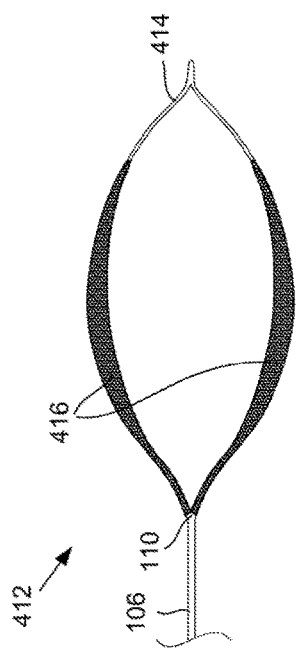

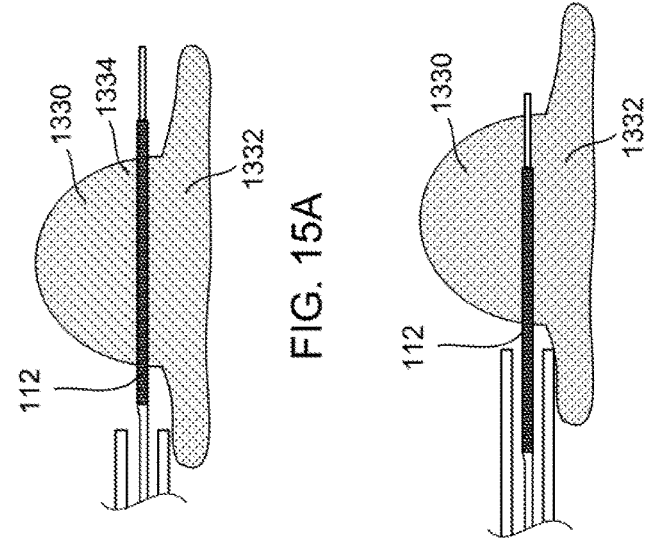
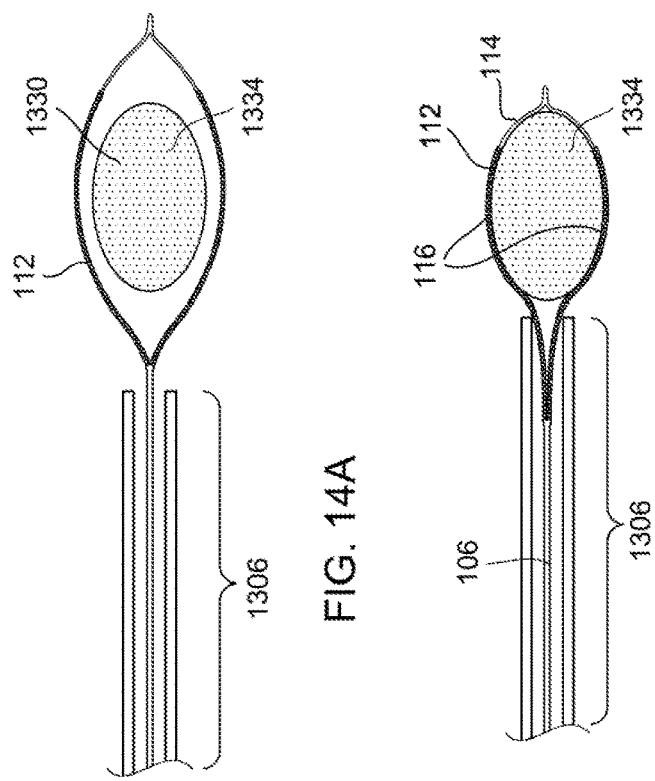

VARIABLE THICKNESS ELECTROSURGICAL SNARE

CROSS-REFERENCE TO RELATED APPLICATIONS

This application claims the benefit of U.S. Provisional Application No. 62/095,984, filed Dec. 23, 2014. The contents of U.S. Provisional Application No. 62/095,984 are hereby incorporated by reference in their entirety.

TECHNICAL FIELD

The present invention relates generally to medical devices and more particularly to an electrosurgical snare having an uninsulated variable thickness distal loop.

BACKGROUND

Endoscopic snares may be used for tissue resection at a treatment site within a patient. For example, tissue resection may be performed in the gastrointestinal (GI) anatomy of a patient during various procedures, such as endoscopic submucosal dissection (ESD), endoscopic mucosal resection (EMR), and polpectomies. Tissue resection may be performed "hot" (i.e., with application of radio frequency (RF) current) or "cold" (i.e., without application of RF current, or manual resection). During tissue resection, either hot or cold, a distal loop of the snare is placed around a targeted tissue and is then retracted, which applies circumferential force around the tissue. For hot snares, RF current is also applied to the tissue, which cuts the tissue.

Some electrosurgical snares that apply RF current to the targeted tissue have a distal loop that is uninsulated. As such, RF current that is supplied to the distal loop is spread out along the entire length of the exposed wire that is in contact with the tissue. In addition, the wire making up the distal loop may have a constant diameter or thickness, and so the RF current may be distributed evenly (i.e., the current density may be the same) over the portions of the distal loop in contact with the tissue since the thickness and corresponding surface area are the same. If power settings of the power source generating the RF current are too low, the current density over the portions of the distal loop in contact with the tissue may be correspondingly too low, which makes it difficult and/or time consuming to initiate cutting the targeted tissue.

In addition, when the current density is too low, rather than cut the tissue, the RF current may coagulate the tissue, which may leave a ring of coagulation, even when the targeted tissue is finally cut. The ring of coagulation may make it difficult for a pathologist or a histologist to determine margins of the lesion. Also, a portion of the ring of coagulation that is left as part of the tissue in vivo may slow down tissue regeneration to cover the exposed muscle bed, which could result in delayed perforations.

While circumferentially coagulating the targeted tissue for a prolonged period of time prior to cutting may be undesirable, immediately circumferentially cutting the tissue once the RF current is applied may also be undesirable as doing so may lead to excessive bleeding. Hence, achieving a suitable balance of cutting and coagulation circumferentially around the targeted tissue during the resection process may be desirable in order to avoid both excessive coagulation and excessive bleeding.

BRIEF SUMMARY

In a first aspect, an electrosurgical snare may include an elongate conductive member longitudinally extending from a proximal end to a distal end; and a conductive distal loop connected to the distal end of the elongate member. The distal loop may include a first uninsulated portion having a first outer diameter, and a second uninsulated portion having a second outer diameter. The second outer diameter may be greater than the first outer diameter.

In a second aspect, a method of performing tissue resection may include: delivering a conductive distal loop of an electrosurgical snare to a treatment site within a patient, where the distal loop may include a thinner uninsulated portion having a first outer diameter and a thicker uninsulated portion having a second outer diameter. The second outer diameter may be greater than the first outer diameter. The method may also include: positioning the distal loop around a target tissue portion of underlying tissue to be resected, contacting a first portion of the target tissue portion with the thinner uninsulated portion and a second portion of the target tissue with the thicker uninsulated portion, applying electrical current to the target tissue portion with both the thinner uninsulated portion and the thicker uninsulated portion of the distal loop, and retracting the distal loop into a lumen of an elongate tubular member upon applying electrical current to the target tissue portion.

In a third aspect, an electrosurgical device may include: an elongate tubular member longitudinally extending from a proximal portion to a distal portion, where the elongate tubular member may include a body and a lumen longitudinally extending in the body. The electrosurgical device may further include an electrosurgical snare longitudinally and movably disposed in the lumen. A distal conductive loop of the electrosurgical snare may include a thinner uninsulated portion and a thicker uninsulated portion.

BRIEF DESCRIPTION OF THE DRAWINGS

FIG. 2 is a top view of a second example configuration of the variable thickness distal loop.

FIG. 3 is a top view of a third example configuration of the variable thickness distal loop.

FIG. 4 is a top view of a fourth example configuration of the variable thickness distal loop.

FIG. 5 is a top view of a fifth example configuration of the variable thickness distal loop.

FIG. 14A is a top view of the variable thickness distal loop positioned around a target tissue portion.

FIG. 14B is a top of the variable thickness distal loop being adjusted around the target tissue portion.

FIG. 15A is a side view of variable thickness distal loop positioned around the target tissue portion, corresponding to the top view of FIG. 13A.

FIG. 15B is a side view of the variable thickness distal loop being adjusted around the target tissue portion, corresponding to the top view of FIG. 13B.

DETAILED DESCRIPTION

The present description describes medical devices and related systems and methods that include an electrosurgical snare that has a distal loop having multiple uninsulated portions, where at least one of the uninsulated portions has an outer diameter or thickness that is greater than an outer diameter or thickness of another of the uninsulated portions. The thicker portion may have a correspondingly larger surface area than the thinner portion.

During a tissue resection procedure of a target tissue portion from underlying tissue, both the portion with the larger diameter and the tissue with the smaller diameter may initially contact the target tissue portion. When electrical current is delivered to the distal loop, the current density over the thicker portion may be smaller than the current density over the thinner portion. As a result, a part of the target tissue portion contacting the thicker portion of the distal loop may begin being coagulated while a part of the target tissue portion contacting the thinner portion of the distal loop may begin being cut. The distal loop may be retracted, causing the thinner portion to continue to cut more tissue while less and less of the thicker portion contacts the tissue. Parts of the target tissue portion that were initially coagulated may not bleed as much when they are subsequently cut, as opposed to if those parts were cut without ever being coagulated.

Figure 1:
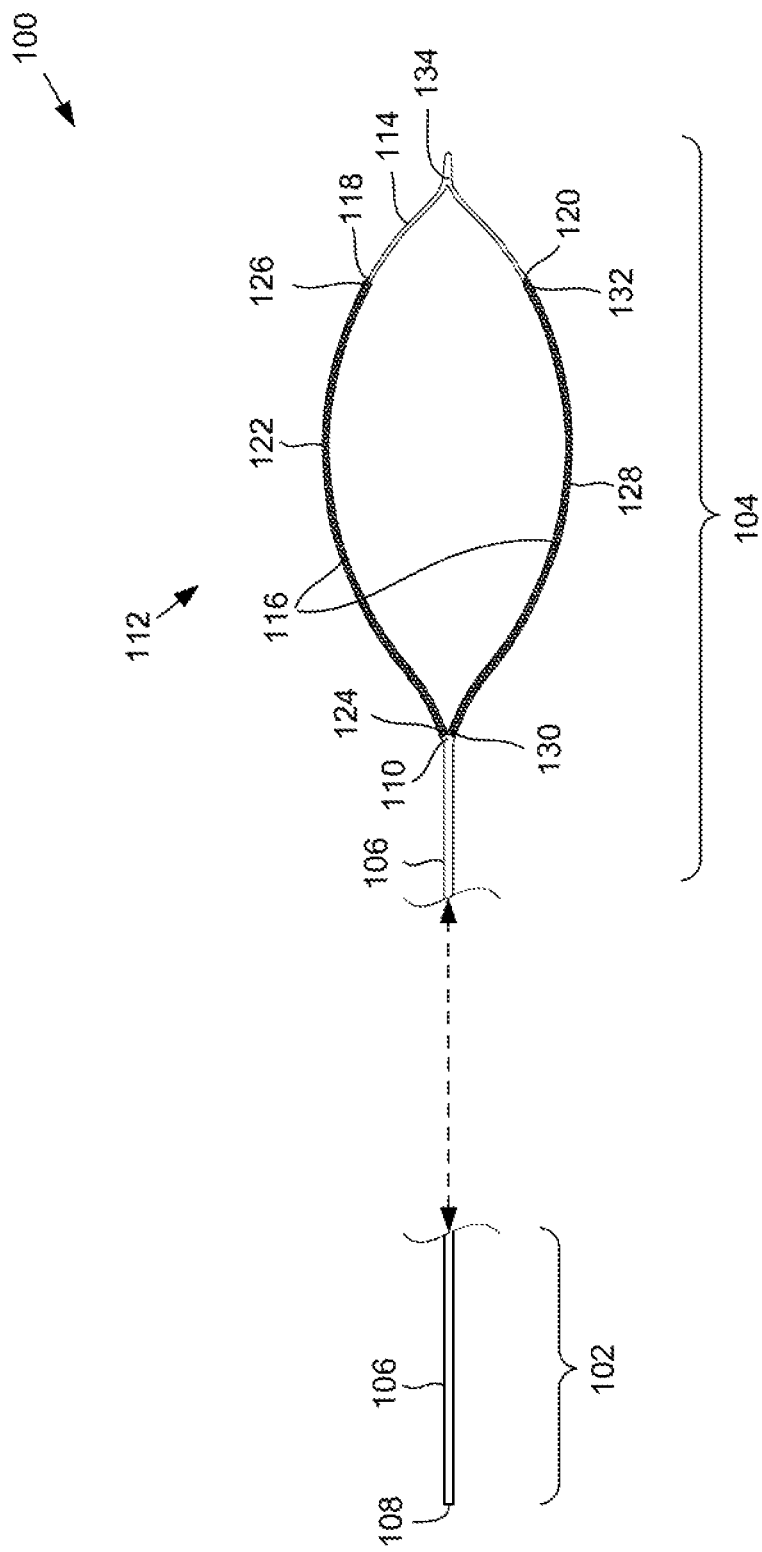
FIG. 1 is a top view of an example electrosurgical snare, showing a first example configuration of a variable thickness distal loop.

FIG. 1 shows a top view of an electrosurgical snare 100 longitudinally extending from a proximal portion 102 to a distal portion 104. The snare 100 may include an elongate conductive member 106 that longitudinally extends from a proximal end 108 to a distal end 110. The snare 100 may also include a conductive distal loop 112 connected to the distal end 110 of the elongate member 106. The distal loop 112 may include a plurality of portions, including a first portion 114 and a second portion 116 having different outer diameters or thicknesses from each other. In particular, the first portion 114 may have a smaller diameter and/or may be thinner than the second portion 116. For clarity, the first portion 114 and the second portion 116 are hereafter referred to as the thinner portion 114 and the thicker portion 116, respectively.

Both the thinner portion 114 and the thicker portion 116 may be uninsulated. That is, both the thinner portion 114 and the thicker portion 116 may not be covered by an insulating material. Instead, the conductive outer surfaces of the thinner and thicker portions 114, 116 may be exposed to and capable of contacting their outer surroundings.

For the example configuration of the distal loop 112 shown in FIG. 1, the thinner portion 114 may be a single segment that extends from a first end 118 to a second end 120. The thinner portion 114 may be completely uninsulated and have the same or substantially the same diameter or thickness from the first end 118 to the second end 120. In addition, the thicker portion 116 may include two segments, including a first segment 122 that extends from a first end 124 to a second end 126, and a second segment 128 that extends from a first end 130 to a second end 132. The first ends 124, 130 of the first and second segments 122, 128 may connected to each other and/or each be connected to the distal end 110 of the elongate member 106 or otherwise extend from the distal end 110. From the distal end 110, each of the first and second segments 122, 128 may branch away from each other and extend separately to different ends 118, 120 of the thinner portion 114. As shown in FIG. 1, the second end 126 of the first segment 122 may be connected to the first end 118 of the thinner portion 114, and the second end 132 of the second segment may be connected to the second end 120 of the thinner portion 114. Additionally, like the single-segmented thinner portion 114, the first and second segments 122, 128 may be completely uninsulated and have the same or substantially the same diameter or thickness as they extend from their respective first ends 124, 130 to respective second ends 126, 132.

In addition, for the example configuration of the distal loop 112, the thinner portion 114 may include an apex or cutting tip 134 of the distal loop 112. The apex 134 may be the portion of the distal loop 112 that biases a target tissue portion in the direction in which the snare 100 is being withdrawn to resect the tissue. For the example configuration shown in FIG. 1, during a resection procedure, the distal loop 112 may be proximally withdrawn to resect a target tissue portion, and the apex 134 may include a distal-most tip that proximally biases the target tissue portion as the distal loop 112 is proximally withdrawn. Additionally, the inner-part or surface of the apex may be the last part of the distal loop 112 to contact and cut target tissue during a resection operation. For the configuration shown in FIG. 1, the inner-part or surface of the apex 134 may include a V-shaped or other-similar shaped surface to grasp or secure the target tissue in contact with the thinner portion 114 as the distal loop 112 is proximally retracted during the resection operation. Additionally, FIG. 1 shows the apex 134 being centrally located along the thinner portion 114—i.e., the length from the apex 134 to the first end 118 is about the same as the length from the apex 134 to the second end 120. For alternative configurations, the apex 134 may be an off-centered part of the thinner portion 134—i.e., the length from the apex 134 to the first end 118 may be different (longer or shorter) than the length from the apex 134 to the second end 120.

FIGS. 2-9 show other example configurations of distal loops having a thinner portion and a thicker portion, each of which may be connected to the distal end 110 of the elongate member 106 instead of the distal loop 112. Referring to FIG. 2, a distal loop 212 may include first ends 224, 230 of first and second segments 222, 228 of an uninsulated thicker portion 216 that are not directly connected to the distal end 110 of the elongate member 106. Instead, the distal loop 212 may include a third uninsulated segment 236 that connects the first end 224 of the first segment 222 to the distal end 110, and an uninsulated fourth segment 238 that connects the first end 230 of the second segment 228 to the distal end 110, where each of the third segment 236 and a fourth segment 238 has a diameter that is less than the diameter of the thicker portion 216.

Referring to FIG. 3, for another example distal loop configuration, a distal loop 312 may include first ends 324, 330 of first and second segments 322, 328 of an uninsulated thicker portion 316 that are not directly connected to the distal end 110 of the elongate member 106. Instead, the distal loop 312 may include a first insulated segment 340 that connects the first end 324 of the first segment 322 to the distal end 110, and a second insulated segment 342 that connects the first end 330 of the second segment 328 to the distal end 110. By being insulated, the first and second insulated segments 340, 342 may have an outer surface that is not capable of delivering electrical current to tissue they are in contact with. However, the first and second insulated segments 340, 342 may have conductive cores that communicate the electrical current from the elongate member 106 to the uninsulated thicker portion 316 of the distal loop 312.

Referring to FIG. 4, for another example distal loop configuration, a distal loop 412 may include a thicker portion 416 having a variable diameter or thickness. For configurations where the diameter or thickness varies, the diameter or thickness may be the average diameter or thickness over its length. In addition or alternatively, a minimum diameter or thickness of the thicker portion 416 may be greater than a maximum diameter or thickness of the thinner portion 414.

Referring to FIG. 5, for another example distal loop configuration, a thicker portion of a distal loop 512 may include a plurality of uninsulated segments 544 separated from each other by one or more insulated segments 546.

Figure 6:
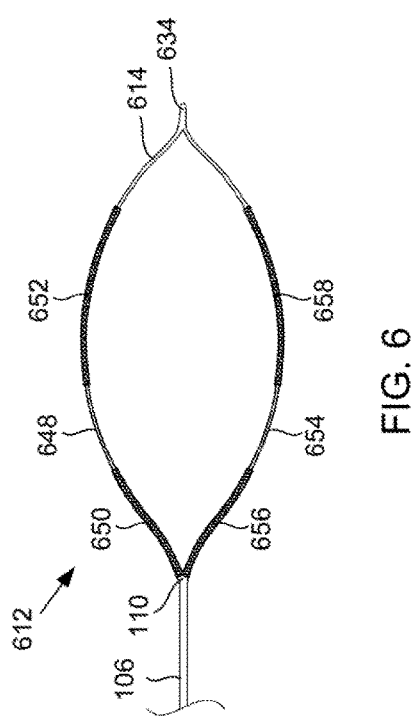
FIG. 6 is a top view of a sixth example configuration of the variable thickness distal loop.

Referring to FIG. 6, for another example distal loop configuration, a thinner portion of a distal loop 612 may include a plurality of segments, including a first segment 614 that includes an apex 634 of the distal loop 612 and at least one additional segment separate or discontinuous from the first segment 614 that separates and/or is disposed in between two segments of a thicker portion. For example, as shown in FIG. 6, a second thinner segment 648 discontinuous from the first thinner segment 614 may separate and/or be disposed in between a first thicker segment 650 and a second thicker segment 652, and a third thinner segment 654 discontinuous from the first thinner segment 614 may separate and/or be disposed in between a third thicker segment 656 and a fourth thicker segment 658.

Figure 7:
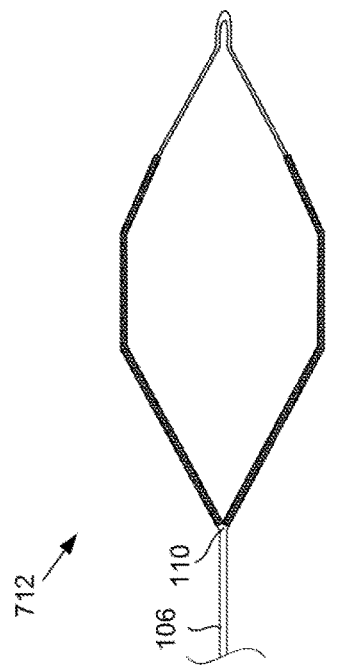
FIG. 7 is a top view of a seventh example configuration of the variable thickness distal loop.
Figure 8:
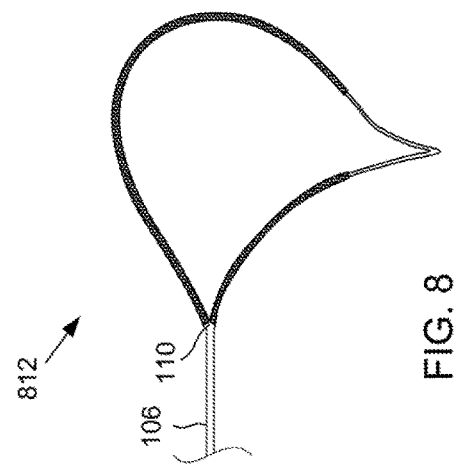
FIG. 8 is a top view of an eighth example configuration of the variable thickness distal loop.

The example distal loops 112, 212, 312, 412, 512, and 612 shown in FIGS. 1-6 have an oval-shaped loop. However, shapes for the distal loop other than oval-shaped may be possible. For example, FIG. 7 shows an example distal loop 712 having a hexagonal shape. As another example, FIG. 8 shows an example distal loop 812 having a duck-billed shape. Other shapes for the distal loop may be possible.

Figure 10:
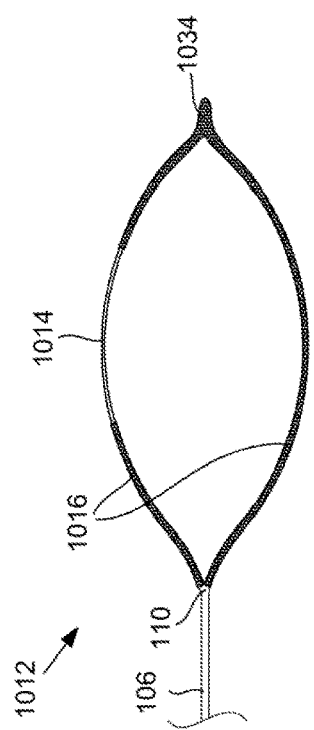
FIG. 10 is a top view of a tenth example configuration of the variable thickness distal loop.
Figure 9:
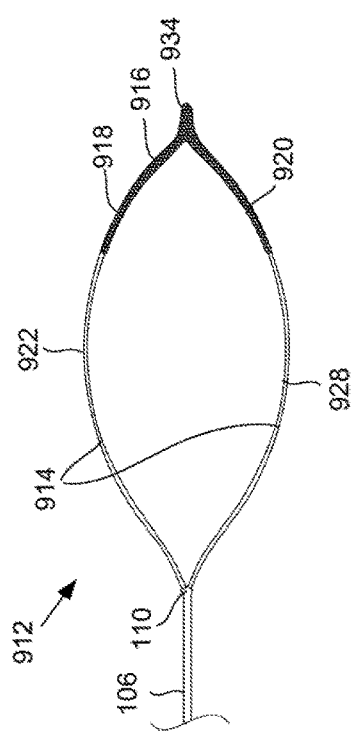
FIG. 9 is a top view of a ninth example configuration of the variable thickness distal loop.

In addition, in each of the example distal loops 112, 212, 312, 412, 512, 612, 712, and 812 shown in FIGS. 1-8, the apex is part of the thinner portion. FIGS. 9 and 10 show other embodiments where the apex is part of the thicker portion. Referring to FIG. 9, a distal loop 912 is similar to the distal loop 112 of FIG. 1, except that thinner and thicker portions 914, 916 are reversed from the thinner and thicker portion 114, 116 of FIG. 1. The thicker portion 916 may be a single segment that includes an apex 934, whereas the thinner portion 914 may include two segments, including a first segment 922 and a second segment 928 each connected to the distal end 110 of the elongate conductive member 106, and branching away from each other as they distally extend separately to different ends 918, 920 of the thicker portion 916.

Referring to FIG. 10, for another example distal loop configuration, a thicker portion 1016 of a distal loop 1012 may include an apex 1034 as well as other portions of the distal loop 1012, except for a thinner portion 1014, which may include a single segment extending in between the distal portion 110 and the apex 1034.

The example configurations for a distal loop of a snare shown and described with reference to FIGS. 1-10 are non-limiting examples. Other distal loop configurations may be possible, including those that combine the different features of the different distal loop configurations shown and described with reference to FIGS. 1-10.

For any of the previously-described example distal loop configurations, the thinner uninsulated portion and the thicker uninsulated portion may each have an associated diameter or thickness. For each of the uninsulated portions, if the associated diameter or thickness varies over its length, then the associated diameter or thickness may be the average diameter or thickness over the length. At a minimum, a ratio of the diameter or thickness of the thicker uninsulated portion to the diameter or thickness of the thinner portion may be greater than one-to-one. For some example configurations, the diameter or thickness ratio may be in a range from about one and one-tenth to one (1.1:1) to ten-to-one (10:1). For a particular configuration, the diameter of the thinner portion may be about 0.005 inches (about 0.127 millimeters) and the diameter of the thicker portion may be about 0.025 inches (about 0.635 millimeters).

In addition or alternatively, for any of the previously-described example distal loop configurations, the thinner uninsulated portion and the thicker uninsulated portion may each have an associated surface area of its respective outer surface. Where an uninsulated portion includes multiple segments, the surface area for that uninsulated portion may be a total surface area, which may be the sum of the surface areas of the segments. At a minimum, a ratio of the surface area of the thicker uninsulated portion to the surface area of the thinner uninsulated portion may be greater than one-to-one. For some example configurations, the surface area ratio may be in a range from about one and one-tenth to one (1.1:1) to ten-to-one (10:1).

In addition or alternatively, for any of the previously-described example distal loop configurations, the thinner uninsulated portion and the thicker uninsulated portion may each have an associated length. Where an uninsulated portion includes multiple segments, the length for that uninsulated portion may be a total length, which may be the sum of the lengths of the segments. At a minimum, a ratio of the length of the thicker uninsulated portion to the length of the thinner uninsulated portion may be greater than or equal to one-to-one. For some example configuration, the length ratio may be in a range from about one-to-one (1:1) to four-to-one (4:1).

Figure 12:
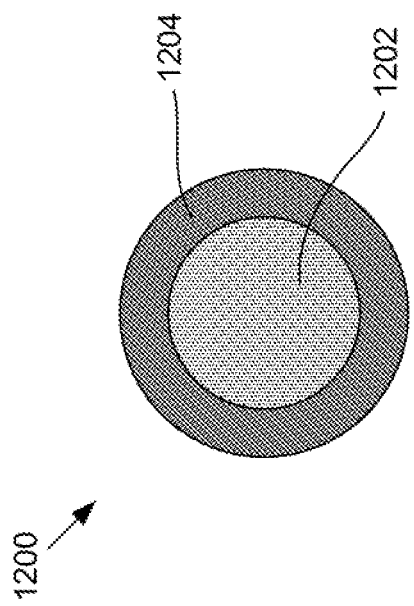
FIG. 12 is a cross-sectional view of another example cross-section of the thicker portion of the variable thickness distal loop.
Figure 11:
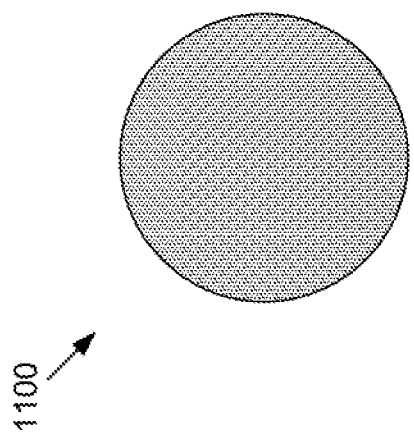
FIG. 11 is a cross-sectional view of an example cross-section a thicker portion of the variable thickness distal loop.

FIGS. 11 and 12 show cross-sectional views of example cross-sections of thicker uninsulated portions 1100, 1200, respectively, each of which may be representative of a cross-section for any of the thicker portions shown and described with reference to FIGS. 1-10. Referring to FIG. 11, the thicker uninsulated portion 1100 may be made of a single conductive material, which may be the same as or different from the conductive material used for the thinner uninsulated portion. Referring to FIG. 12, the thicker uninsulated portion 1200 may be made of a plurality of different conductive materials. For example, the thicker uninsulated portion 1200 may include an inner conductive core 1202 made of a first conductive material, and a second outer conductive member 1204 made of a second conductive material. For some example configurations, the second conductive material for the outer member 1204 may have a higher resistivity than the first conductive material for the inner core 1202. Additionally, the inner core 1202 may be made of the same conductive material as the thinner uninsulated portion. The higher resistivity of the second conductive material of the outer member compared to the first conductive material of the inner core and thinner uninsulated portion may provide an increased current density of current flowing along the outer surface of the thinner uninsulated portion relative to the current density of current flowing along the outer surface of the thicker uninsulated portion.

Figure 13:
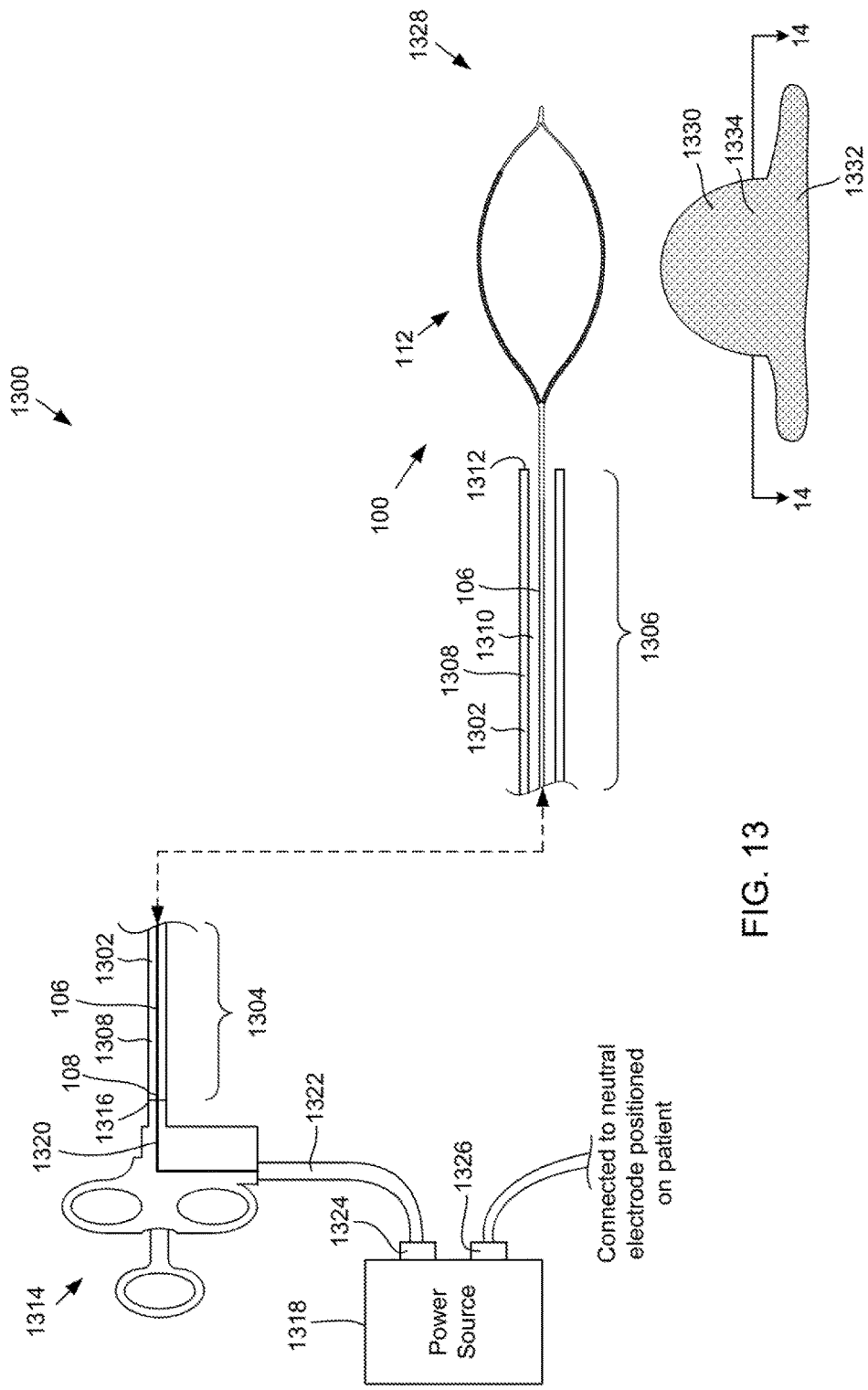
FIG. 13 is partial cross-sectional side view of an example medical system that includes an electrosurgical snare.

FIG. 13 shows a partial cross-sectional side view of a medical system 1300, such as an endoscopic medical system, with which the electrosurgical snare 100 may be implemented. FIG. 13 shows the electrosurgical snare 100 as having the configuration of the distal loop 112 as shown and described with respect to FIG. 1, although a snare having any of the other distal loop configurations 212-1012 shown and described with respect to FIGS. 2-10 may be similarly included as part of the medical system 1300.

In addition to the medical snare 100, the medical system 1300 may include an elongate tubular member 1302, such as a catheter, endoscope, or other similar elongate tubular structure, that extends from a proximal portion 1304 to a distal portion 1306. The tubular member 102 may include a body 1308 extending from the proximal portion 1304 to the distal portion 1306, and a lumen 1310 longitudinally extending in the body 1308 (For purposes of clarity, the lumen 1310 is not shown extending in the proximal portion 1304). For some example configurations, the lumen 1310 may be a single lumen of the tubular member 1302. For other example configurations, the lumen 1310 may be one of a plurality of lumens of the tubular member 1302.

The electrosurgical snare 100 may be longitudinally and movably disposed in the lumen 1310. In particular, the snare 100 may be movable between an undeployed position and a deployed position. In the undeployed, the distal loop 112 may be disposed in the lumen 1310 at the distal portion 1306. In the deployed position, the distal loop may be disposed outside of the lumen 1310 past a distal end 1312 of the tubular member 1302. FIG. 12 shows the electrosurgical snare 100 in the deployed position.

The medical system 1300 may further include a handle assembly 1314 coupled to a proximal end 1316 of the tubular member 1302. The handle assembly 1314 may be operatively coupled to the proximal end 108 of the elongate member 106, and configured to move the snare 100 between the deployed and undeployed positions. FIG. 13 shows the handle assembly 1314 configured as a three-ringed structure for gripping by an operator of the medical system 1300, although other configurations for the handle assembly 1314 may be possible.

In addition, the medical system 1300 may include a power source 1318, such as a radio frequency (RF) generator or an electrosurgical unit (ESU), electrically coupled to the electrosurgical snare 100. As shown in FIG. 13, the electrosurgical snare 100 may be electrically coupled to the power source 1318 via the handle assembly 1314, which may include a conductive member 1320 integrated with the three-ring assembly an electrical cabling 1322 that electrically couples the handle assembly 1314 with an active port 1324 of the power source 1318.

The electrosurgical snare 100 may be part of an active path that supplies electrical current to a target tissue portion of underlying tissue at a treatment site within a patient to perform an electrosurgical procedure on the target tissue portion. The power source 1318, when activated, may deliver the electrical current to the electrosurgical snare 100. For the configuration shown in FIG. 13, the electrosurgical snare 100 may be electrically coupled to the power source 1318 in a monopolar configuration, in which a return path for the medical system 1300 may include a neutral electrode (not shown) positioned on the patient and electrically coupled to a return port 1326 of the power source 1318. For other example configurations, the electrosurgical snare 100 may have a bipolar configuration with the power source 1318, in which the return path may extend within and/or alongside the elongate tubular member 1302 back to the return port 1326.

Additionally, other example medical systems may include more or fewer than the components shown in FIG. 13. For example, an electrosurgical medical device may include the electrosurgical snare 100 and the elongate tubular member 1302, and may or may not include the handle assembly 1314. The electrosurgical medical device may be removably connected with the power source 1318 and/or may perform several electrosurgical procedures with different power sources. Various configurations or combinations of the example medical system 1300 and/or various systems in which the electrosurgical snare 100 may be implemented may be possible.

The following describes an example method of performing a tissue resection operation using the medical system 1300. Description of the method is made with reference to FIGS. 13, 14A-E, and 15A-E. Referring to FIG. 13, the tissue resection operation may be performed to remove a target tissue portion 1330 of underlying tissue 1332 at a treatment site 1328 within a patient. The target tissue portion 1230 may be a polyp, pseudopolyp, or other raised portion of tissue for which a snare may be suitable for its removal and/or resection.

FIG. 13 shows the distal portion 1306 of the tubular member 1302 along with the distal loop 112 delivered to the treatment site 1328. FIGS. 14A-14E show a top view of the distal loop 112, the distal portion 1306 of the tubular member 1302, and a cross-section of a base portion 1334 of the target tissue portion 1330 taken along line 14-14 during the resection operation. FIGS. 15A-15E correspond to FIGS. 14A-14E, and show a side view of the distal loop 112 during the resection operation of the target tissue portion 1330.

As shown in FIGS. 14A and 14A, the distal loop 112 may be positioned around the base portion 1334 of the target tissue portion 1330. As shown in FIGS. 14B and 15B, the distal loop 112 and distal portion 1306 may be moved to secure the distal loop 112 around the base portion 1334 and/or to optimize the amount of contact each of the thinner portion 114 and the thicker portion 116 of the distal loop 112 makes with the target tissue portion 1330.

After positioning the distal loop 112 in a desired position around the base portion 1334, the power source 1318 may be activated, and electrical current may be delivered from the power source 1318, through the elongate conductive member 106 of the snare 100, to the distal loop 112, which may apply the electrical current to the base portion 1334. Additionally, the surface area of the thinner portion 114 may be in a range such that application of the electrical current to the base portion 1334 by the thinner portion 114 has the effect of cutting the part of the base portion 1334 in contact with the thinner portion 114. Further, the surface area of the thicker portion 116 may be in a range such that application of the electrical current to the base portion 1334 by the thicker portion 116 has the effect of coagulating the part of the base portion 1334 in contact with the thicker portion 116.

Figure 15C:
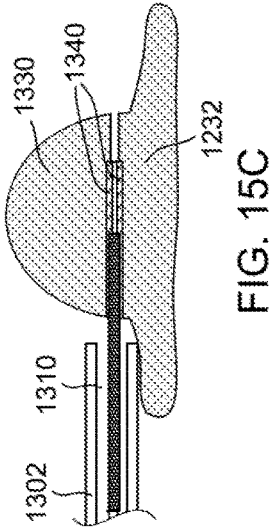
FIG. 15C is a side view of the variable thickness distal loop having partially cut the target tissue portion, corresponding to the top view of FIG. 13C.
Figure 14C:
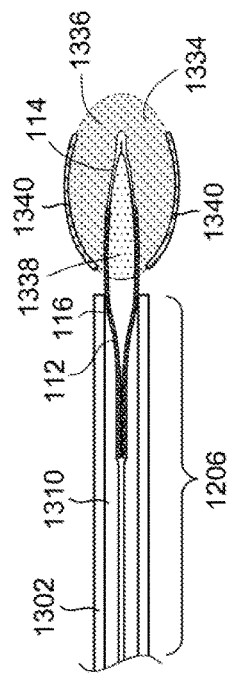
FIG. 14C is a top view of the variable thickness distal loop having partially cut the target tissue portion.

Referring to FIGS. 14C and 15C, upon activation of the power source 1318 and application of the electrical current to the base portion 1334 of the target tissue 1330, the handle assembly 1314 may be operated to retract the distal loop 112 to within the lumen 1310. As shown in FIG. 13C, as the distal loop 112 is retracted to within the lumen 1310, the diameter of the distal loop 112 may decrease, collapsing the distal loop 112 inward. For some example methods, the thicker portion 116 may begin cutting the base portion 1334 it comes into contact with after the initial application of the electrical current. For other example methods, the thicker portion 116 may continue to coagulate the tissue it contacts. However, the base portion 1334 may be squeezed inwardly or compressed due to the shrinking size of the distal loop 112, decreasing the circumference and/or cross-section of the base portion 1334 and allowing the thinner portion 114 to cut more and more of the base portion 1334 as the distal loop 112 is retracted. The darker shading with the dotted lines outside of the distal loop 112 shows an area 1336 of the base portion 1334 remaining with the underlying tissue 1332 after cutting, and the lighter shading inside the loop 112 shows an area 1338 of the base portion 1334 that has not yet been cut.

Additionally, FIGS. 14C and 14C show coagulated tissue 1340 along parts of the edges of both the target tissue portion 1330 and the base portion 1334 remaining with the underlying tissue 1332 after cutting that were initially in contact with the thicker portion 116 upon application of the electrical current. Coagulating some of the base portion 1334 first before cutting may reduce the amount of bleeding during the resection process, compared to if the distal loop 112 only cut the tissue. At the same time, by initially cutting at least some of the base portion 1334 using the thinner portion 114 without first coagulating may provide an overall better tissue sample for histopathological evaluation, than if an entire ring of coagulation formed around the target tissue portion 1330.

Figure 15D:
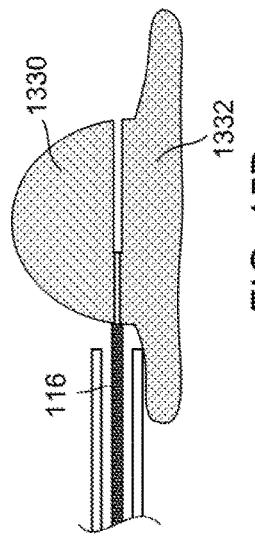
FIG. 15D is a side view of the thinner portion of the variable thickness distal loop solely being in contact with the tissue, corresponding to the top view of FIG. 13D.
Figure 15E:
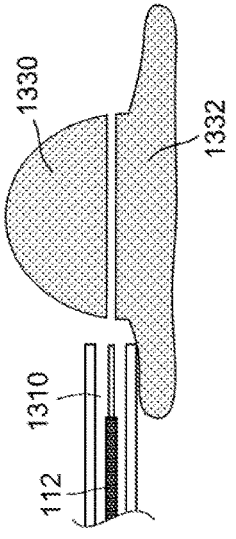
FIG. 15E is a side view of the variable thickness distal loop having completely resected the target tissue portion, corresponding to the top view of FIG. HE.
Figure 14D:
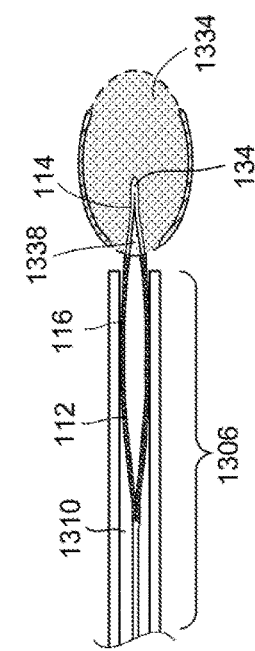
FIG. 14D is a top view of the variable thickness distal loop having further cut the target tissue portion, where only a thinner portion is in contact with the target tissue portion.
Figure 14E:
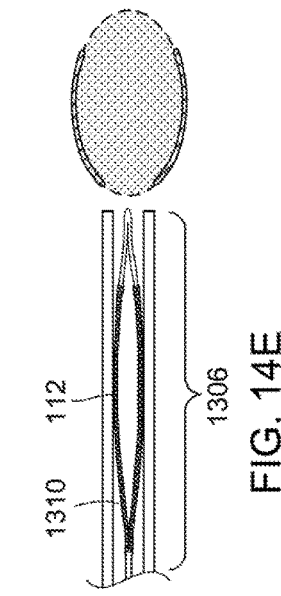
FIG. 14E is a top view of the variable thickness distal loop having completely resected the target tissue portion.

Further, as shown in FIGS. 14C and 15C, a ratio of the surface area of the thicker portion 116 in contact with the target tissue 1330 to the surface area of the thinner portion 114 in contact with the target tissue (i.e., the contact surface area ratio) may decrease as the distal loop 112 is withdrawn into the lumen and the amount of surface area of the thicker portion 116 in contact with the target tissue 1330 continually decreases as more and more of the distal loop 112 is retracted to within the lumen 1310. FIGS. 14D and 15D show the thicker portion 116 no longer in contact with the base portion 1334 and a small amount of an area 1338 remaining to be cut in contact solely with the thinner portion 114. As the distal loop 112 is being retracted, the apex 134 may grasp or secure the remaining parts of the base portion 1334 in contact with the thinner portion 114. FIGS. 14E and 15E show the distal loop 112 being completely moved to within the lumen 1310 and the target tissue portion 1330 being completely resected from the underlying tissue 1332.

The example method described with reference to FIGS. 13, 14A-E, and 15A-E are described as being performed with a distal loop having a configuration where the apex 134 is part of the thinner portion 114. As mentioned, other variable thickness distal loop configurations, such as those shown in FIGS. 2-10, may be used to similarly perform the resection method. For distal loop configurations where the apex is part of the thicker portion, such as those shown in FIGS. 9 and 10, the apex may begin coagulating the part of the target tissue portion 1330 it is in contact with, while the thinner portion of the distal loop may begin cutting the part(s) of the target tissue portion 1330 it is in contact with. When the resection method is performed with these distal loop configurations, as the distal loop is withdrawn to within the lumen 1310, the amount of surface area of the thinner portion in contact with the target tissue portion 1330 decreases, causing the contact surface area ratio to increase. Eventually, only the thicker portion is in contact with an uncut portion of the target tissue portion 1330. At some point, the contact surface area ratio is high enough that the thicker portion is cutting, rather than coagulating, the target tissue portion 1330.

For some example methods, using a distal loop configuration where the apex is part of the thicker portion instead of the thinner portion may be advantageous, at least for visualization purposes. As shown in FIGS. 13, 14A-E, and 15A-E, the apex 134 may be the distal-most portion of the distal loop 112 and furthest away from the distal end 1312 of the elongate tubular member 1302 when the distal loop 112 is positioned around the target tissue portion 1330. Although not show, an imaging sensor or camera may be positioned near the distal end 1312, such as one mounted on a distal end of an endoscope, and be configured to provide visualization access to an operator or physician of the resection method being performed. When the distal loop 112 is positioned around the target tissue portion 1330 as shown in FIGS. 13, 14A, 15A, the target tissue portion 1330 may block the imaging sensor from being able to visualize the thinner portion 114. As such, when the cutting is being performed, the imaging sensor may not be able to visualize the thinner portion 114 cutting the target tissue portion 1330, but may be able to visualize the thicker portion 116 coagulating the target tissue portion 1330. In contrast, if the thicker portion includes the apex and the thinner portion include the other portions of the distal loop, such as the distal loop configuration shown in FIG. 9, then the imaging sensor may be able to visualize the cutting. Visualizing the cutting rather than the coagulating of the target tissue portion may be desirable during performance of at least some resecting methods.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method of performing tissue resection, the method comprising:

delivering a conductive distal loop of an electrosurgical snare to a treatment site within a patient, wherein the distal loop comprises a thinner uninsulated portion having a first outer diameter and a thicker uninsulated portion having a second outer diameter, the second outer diameter being greater than the first outer diameter;

positioning the distal loop around a target tissue portion of underlying tissue to be resected;

contacting a first portion of the target tissue portion with the thinner uninsulated portion and a second portion of the target tissue with the thicker uninsulated portion;

applying electrical current to the target tissue portion with both the thinner uninsulated portion and the thicker uninsulated portion of the distal loop;

cutting the first portion of the target tissue portion with the thinner uninsulated portion of the distal loop upon applying the electrical current; and coagulating before cutting the second portion of the target tissue portion with the thicker uninsulated portion upon applying the electrical current; and retracting the distal loop into a lumen of an elongate tubular member upon applying the electrical current to the target tissue portion.

2. The method of claim 1, wherein a contact surface area ratio of an amount of surface area of the thicker uninsulated portion in contact with the target tissue portion to an amount of surface area of the thinner uninsulated portion in contact with the target tissue portion decreases as the distal loop is retracted into the lumen.

3. The method of claim 1, wherein a contact surface area ratio of an amount of surface area of the thicker uninsulated portion in contact with the target tissue portion to an amount of surface area of the thinner uninsulated portion in contact with the target tissue portion increases as the distal loop is retracted into the lumen.

4. The method of claim 1, further comprising:

contacting a last portion of the target tissue portion solely with the thinner uninsulated portion of the distal loop before the target tissue portion is completely resected from the underlying tissue.

* * * * *